US00PP33400P2

(12) United States Plant Patent
Solano Ramirez

(10) Patent No.: US PP33,400 P2
(45) Date of Patent: Aug. 24, 2021

(54) ***PETUNIA* PLANT NAMED 'BALVOGITE'**

(50) Latin Name: ***Petunia* x *hybrida***
Varietal Denomination: Balvogite

(71) Applicant: Ball Horticultural Company, West Chicago, IL (US)

(72) Inventor: Rolando Solano Ramirez, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/190,053

(22) Filed: Mar. 2, 2021

(51) Int. Cl.
*A01H 5/02* (2018.01)
*A01H 6/82* (2018.01)

(52) U.S. Cl.
USPC ..... Plt./356.12

(58) Field of Classification Search
USPC ..... Plt./263.1, 356.1, 356.12, 356.15
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Petunia* plant named 'Balvogite', characterized by its semi-double type, white-colored flowers, medium green-colored foliage, and moderately vigorous, mounded-spreading growth habit, is disclosed.

1 Drawing Sheet

Latin name of genus and species of plant claimed: *Petunia* x *hybrida*.
Variety denomination: 'Balvogite'.

BACKGROUND OF THE INVENTION

The present invention relates to a new and distinct cultivar of *Petunia* plant botanically known as *Petunia* x *hybrida* and hereinafter referred to by the cultivar name 'Balvogite'.

The new cultivar originated in a controlled breeding program in Guadalupe, Calif. during July 2017. The objective of the breeding program was the development of semi-double type *Petunia* cultivars that have a mounded-spreading growth habit.

The new *Petunia* cultivar is the result of cross-pollination. The female (seed) parent of the new cultivar is the proprietary *Petunia* x *hybrida* breeding selection coded 09W-W-21-3, not patented, characterized by its single-type, white-colored, dark green-colored foliage, and vigorous, spreading growth habit. The male (pollen) parent of the new cultivar is DOUBLE WAVE Rose 'Kirimaji Double Rose', U.S. Plant Pat. No. 13,834, characterized by its semi-double type, red-purple colored flowers having brighter red-purple venation, medium green-colored foliage, and vigorous, cascading and prostrate growth habit. The new cultivar was selected as a single flowering plant within the progeny of the above stated cross-pollination during January 2018 in a controlled environment in Guadalupe, Calif.

Asexual reproduction of the new cultivar by terminal stem cuttings since January 2018 in Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balvogite' as a new and distinct cultivar of *Petunia* plant:

1. Semi-double type, white-colored flowers;
2. Medium green-colored foliage; and
3. Moderately vigorous, mounded-spreading growth habit.

Plants of the new cultivar differ from plants of the female parent primarily in having semi-double type flowers, reduced growth vigor, and a more mounded growth habit. Plants of the new cultivar differ from plants of the male parent primarily in having white-colored flowers and a more mounded growth habit.

Of the many commercially available *Petunia* cultivars, the most similar in comparison to the new cultivar is DOUBLE WAVE White 'Kirimaji Double White', U.S. Plant Pat. No. 14,281. However, in comparison, plants of the new cultivar differ from plants of 'Kirimaji Double White' in at least the following characteristics:

1. Plants of the new cultivar are narrower than plants of 'Kirimaji Double White';
2. Plants of the new cultivar have vestigial pistils unlike plants of 'Kirimaji Double White'; and
3. Plants of the new cultivar have faint green-colored midveins on petal upper surface unlike the red-purple colored midveins of plants of 'Kirimaji Double White'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balvogite'. The approximately 14-week-old plants were grown in 6-inch pots for approximately 7 weeks in a greenhouse in West Chicago, Ill. Plants were given one pinch four weeks prior to transplant.

DETAILED BOTANICAL DESCRIPTION

Figure 1:
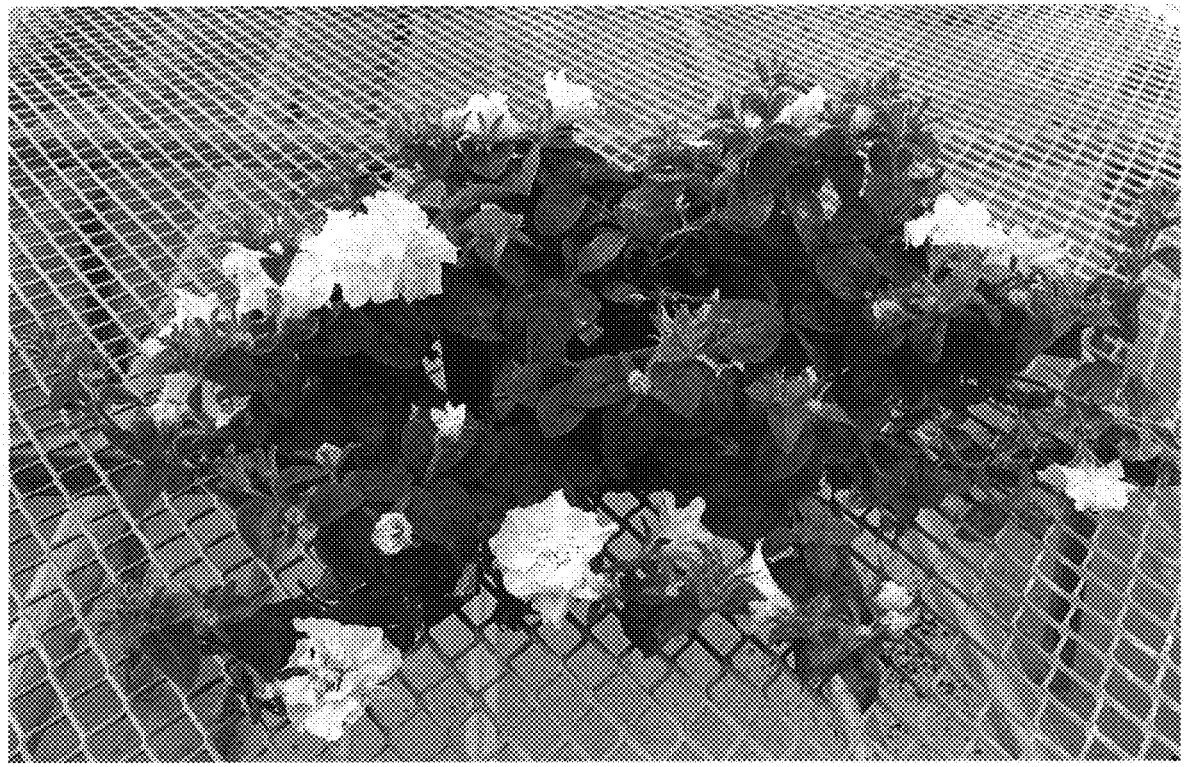
FIG. 1 illustrates a side view of the overall growth and flowering habit of 'Balvogite'.
Figure 2:
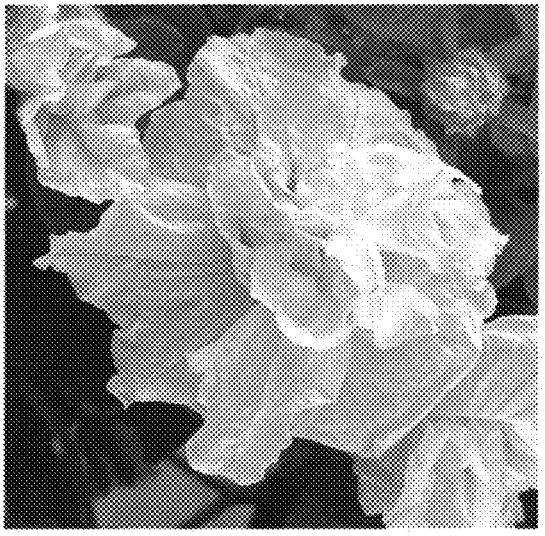
FIG. 2 illustrates a close-up view of an individual flower of 'Balvogite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December 2020 under natural light conditions in West Chicago, Ill.

The following descriptions and measurements describe approximately 14-week-old plants produced from cuttings from stock plants and grown in a glass-covered greenhouse under conditions comparable to those used in commercial practice. The plants were grown in West Chicago, Ill. in 6-inch pots for approximately 7 weeks utilizing a soilless growth medium. Plants were given one pinch four weeks prior to transplant. Greenhouse temperatures were maintained at approximately 70° F. to 75° F. (21° C. to 24° C.) during the day and approximately 68° F. to 74° F. (20° C. to 23° C.) during the night. Supplemental lighting was used. Measurements and numerical values represent averages of typical plants.

Botanical classification: *Petunia* x *hybrida* 'Balvogite'.

Parentage:

*Female parent*.—Proprietary *Petunia* x *hybrida* breeding selection coded 09W-W-21-3, not patented.

*Male parent*.—DOUBLE WAVE Rose 'Kirimaji Double Rose', U.S. Plant Pat. No. 13,834.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Moderately vigorous, mounded-spreading growth habit.

*Size*.—Height from soil level to top of plant plane: Approximately 16.0 cm. Width: Approximately 59.0 cm.

*Branching habit*.—Freely branching. Pinching enhances basal branching. Quantity of main branches per plant: Approximately 8.

*Branch*.—Strength: Moderate. Length: Approximately 33.0 cm. Diameter: Approximately 3.0 mm. Length of central internode: Approximately 2.5 cm. Texture: Densely glandular pubescent with a mixture of long and short hairs. Gland color: Colorless, transparent. Color of young stems: 144A. Color of mature stems: 146A.

Foliage description:

*General description*.—Quantity of leaves per main branch: Approximately 19. Fragrance: Slight. Form: Simple. Arrangement on flowering stem: Alternate.

*Leaves*.—Aspect: Acute angle to perpendicular to stem. Shape: Ovate. Margin: Entire. Apex: Broadly acute. Base: Broadly attenuate to rounded. Venation pattern: Pinnate. Length of mature leaf: Approximately 4.5 cm. Width of mature leaf: Approximately 3.7 cm. Texture of upper surface: Sparsely glandular pubescent. Texture lower surface: Moderately glandular pubescent. Gland color: Colorless, transparent. Color of upper surface of young and mature foliage: 137A with venation of 146C to indistinguishable. Color of lower surface of young and mature foliage: Closest to 146B with venation of 146D to indistinguishable.

*Petiole*.—Length: Approximately 8.0 mm. Width: Approximately 3.0 mm. Texture: Densely glandular pubescent with a mixture of long and short hairs. Gland color: Colorless, transparent. Color: 146D.

Flowering description:

*Flowering habit*.—'Balvogite' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Semi-double, hemispherical. Quantity per plant: Approximately 14. Fragrance: Slight.

*Bud*.—Rate of opening: Generally takes 3 to 5 days for bud to progress from first color to fully open flower. Quantity per plant: Approximately 30.

*Bud just before opening*.—Shape: Ovoid. Length: Approximately 1.7 cm. Diameter at widest point: Approximately 1.2 cm. Diameter at base: Approximately 3.0 mm. Texture: Densely glandular pubescent. Gland color: Colorless, transparent. Color of petal portion: 155C with venation of 144B. Color of tube: 155C with an overlay and venation of 144B.

*Corolla*.—Diameter: Approximately 6.5 cm.

*Petals*.—Quantity: Approximately 21 to 23, base fused to form a tube. Shape: Obovate. Appearance: Matte. Margin: Entire, ruffled. Apex: Broadly acute. Length from throat of outermost: Approximately 2.6 cm. Width of outermost: Approximately 2.3 cm. Length from throat of innermost: Approximately 1.3 cm. Width of innermost when flattened: Approximately 1.0 cm. Texture of upper surface: Glabrous. Texture of lower surface: Sparsely glandular pubescent. Gland color: Colorless, transparent. Color of upper surface when first and fully open: NN155A with faint midveins of 144A. Color of lower surface when first and fully open: NN155A with midveins of 144A.

*Corolla tube*.—Length: Approximately 2.0 cm. Diameter at distal end: Approximately 2.0 cm. Diameter at proximal end: Approximately 3.0 mm. Texture of inner surface: Glabrous. Texture of outer surface: Densely glandular pubescent. Gland color: Colorless, transparent. Color of inner surface: NN155A with an overlay and venation of 144A. Color of outer surface: NN155A with venation of 144A.

*Sepals*.—Quantity per flower: 5, fused at base. Shape: Linear. Margin: Entire. Apex: Broadly acute. Length: Approximately 1.6 cm. Width: Approximately 4.0 mm. Texture of upper and lower surfaces: Densely glandular pubescent. Gland color: Colorless, transparent. Color of upper surface: 137A. Color of lower surface: 138A with 145B at base.

*Peduncle*.—Strength: Strong, flexible. Aspect: Acute angle to stem. Length: Approximately 2.0 cm. Diameter: Approximately 2.0 mm. Texture: Densely pubescent with a mixture of long and short glandular hairs. Gland color: Colorless, transparent. Color: 146C.

*Reproductive organs*.—Androecium: Stamen quantity: Approximately 15 to 17, basifixed. Stamen length (if fully developed): Approximately 1.8 cm. Filament length of fixed portion: Approximately 3.0 mm. Filament color: NN155A to 145D. Anther shape: Bilobed to irregular. Anther length: Approximately 1.0 mm. Anther color: 158B. Pollen amount: Moderate. Pollen color: 155A. Gynoecium: Pistil quantity: 1 per flower, vestigial.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balvogite', substantially as herein illustrated and described.

* * * * *